United States Patent
Mohr et al.

(10) Patent No.: US 10,130,248 B2
(45) Date of Patent: Nov. 20, 2018

(54) METHOD FOR REALIZING OCULAR FUNDUS PHOTOGRAPHS THAT ARE CORRECTED FOR SCATTERED LIGHT

(71) Applicant: Carl Zeiss Meditec AG, Jena (DE)

(72) Inventors: Thomas Mohr, Jena (DE); Michael Kieweg, Berlin (DE)

(73) Assignee: Carl Zeiss Meditec AG, Jena (DE)

( * ) Notice: Subject to any disclaimer, the term of this patent is extended or adjusted under 35 U.S.C. 154(b) by 52 days.

(21) Appl. No.: 14/890,365

(22) PCT Filed: May 15, 2014

(86) PCT No.: PCT/EP2014/059917
§ 371 (c)(1),
(2) Date: Nov. 10, 2015

(87) PCT Pub. No.: WO2014/184279
PCT Pub. Date: Nov. 20, 2014

(65) Prior Publication Data
US 2016/0120400 A1    May 5, 2016

(30) Foreign Application Priority Data
May 17, 2013   (DE) .................. 10 2013 008 532

(51) Int. Cl.
*A61B 3/14* (2006.01)
*A61B 3/00* (2006.01)
(Continued)

(52) U.S. Cl.
CPC .............. *A61B 3/0025* (2013.01); *A61B 3/12* (2013.01); *A61B 3/14* (2013.01); *A61B 5/4842* (2013.01); *A61B 3/1176* (2013.01)

(58) Field of Classification Search
CPC .......... A61B 3/0025; A61B 3/14; A61B 3/102; A61B 3/12; A61B 3/0041; A61B 3/113;
(Continued)

(56) References Cited

U.S. PATENT DOCUMENTS

| 6,419,638 B1 * | 7/2002 | Hay ..................... A61B 3/0025 600/558 |
| 7,147,328 B2 | 12/2006 | Sugino et al. |
| 2012/0229617 A1 * | 9/2012 | Yates ..................... A61B 3/156 348/78 |

FOREIGN PATENT DOCUMENTS

| DE | 101 29 652 A1 | 12/2002 |
| DE | 10 2007 025425 A1 | 12/2008 |

(Continued)

OTHER PUBLICATIONS

Investigating the light absorption in a single pass through the photoreceptor layer by means of lipofuscin fluorescence, In: Vision Research, vol. 45, 2005, p. 1957-1964.*

(Continued)

*Primary Examiner* — Alicia M Harrington
*Assistant Examiner* — Sharrief Broome
(74) *Attorney, Agent, or Firm* — Patterson Thuente Pedersen, P.A.

(57) ABSTRACT

A method by which fundus photographs that are corrected for scattered light can be realised by using a digital fundus camera. The fundus is illuminated and a photograph of the fundus is realized. The photographed area is greater than the illuminated are. The scattered light intensity is determined and is used for correction. Measurement points for determining the scattered light intensity are defined in the non-illuminated area. Values of the scattered light intensity determined at the measurement points are averaged. Average-scattered light intensity thus determined is subtracted from the intensity values of the photograph to correct the photograph.

29 Claims, 2 Drawing Sheets

(51) Int. Cl.
*A61B 3/12* (2006.01)
*A61B 5/00* (2006.01)
*A61B 3/117* (2006.01)

(58) Field of Classification Search
CPC ... A61B 3/1005; A61B 3/0008; A61B 3/0033; A61B 3/0058; A61B 3/0091; A61B 3/1025; A61B 5/4842; A61B 3/032; A61B 3/117; A61B 3/1225; A61B 3/103
USPC .................................................. 351/206, 210
See application file for complete search history.

(56) References Cited

FOREIGN PATENT DOCUMENTS

| | | |
|---|---|---|
| DE | 10 2007 047300 A1 | 4/2009 |
| DE | 10 2007 053386 A1 | 5/2009 |
| EP | 2 668 894 A1 | 12/2013 |
| WO | WO 2009/046912 A1 | 4/2009 |

OTHER PUBLICATIONS

Notification of transmittal of Translation of the International Preliminary Report on Patentability for International Application No. PCT/EP2014/059917, dated Nov. 26, 2015, 16 pages.
PCT International Search Report (12 pages) with English translation (3 pages) for International Application No. PCT/EP2014/059917, dated Nov. 4, 2014.
DE Search Report (5 pages) with English translation (5 pages) for DE 10 2013 008 532.2, dated Sep. 1, 2014.
Anonymous: "Outlier—Wikipedia, the free encyclopedia", , Mar. 14, 2013 (Mar. 14, 2013), XP055132292, Retrieved from the Internet: URL:http://en.wikipedia.org/w/index.php?title=Outlier&oldid=544125593 [retrieved on Jul. 30, 2014].
Prieto, P.M. [et al]: Investigating the light absorption in a single pass through the photoreceptor layer by means of lipofuscin fluorescence. In: Vision Research, vol. 45, 2005, p. 2957-1964.

* cited by examiner

METHOD FOR REALIZING OCULAR FUNDUS PHOTOGRAPHS THAT ARE CORRECTED FOR SCATTERED LIGHT

RELATED APPLICATIONS

This application is a National Phase entry of PCT Application No. PCT/EP2014/059917 filed May 15, 2014, which application claims the benefit of priority to German Application No. 10 2013 008 532.2, filed May 17, 2013, the entire disclosures of which are incorporated herein by reference.

FIELD OF THE INVENTION

The present invention relates to a method with which it is possible to realize ocular fundus images that are corrected for scattered light using a digital fundus camera.

BACKGROUND

As a person's age increases, typically the portion of light that is scattered when it passes through the human eye lens increases, as well. This may cause, inter alia, cloudiness in the eye lens that is also known as a "gray star" or "cataract." Since such cloudiness of the ocular lens very sharply diminishes the person's visual acuity, with older patients frequently the cloudy human lens is replaced by a clear, synthetic intraocular lens.

In every imaging process, cloudiness in the eye lens (cataract), in the vitreous body, and/or in the cornea has a negative impact on image quality in that it scatters both the incident illumination light and the light reflected in the eye. Inclusions or foreign bodies in the eye have the same effect. Even the ophthalmological device itself can cause scattered light, for instance due to soiled optical surfaces. Scattering of light from a cataract is significantly more pronounced for blue light than for light at other wavelengths.

Scattered light that occurs thus also influences the results of important diagnostic procedures. For instance, when measuring the optical density of the macular pigment xanthophyll on the ocular fundus, in accordance with the description of WO 2009/046912 A1, the measured results are distorted due to scattered light that occurs.

WO 2009/046912 A1 suggests a method that determines the macular pigment optical density (MPOD) in the region of the fovea. For this, the brightness curve on the fundus ($I_B$) is determined in the area with no pigment and compared to the actual measured brightness ($I_M$). The optical density of the pigment (OD) is then calculated as follows:

$$OD = 0.5 * \log (I_B/I_M)$$

However, when heavy scattered light $I_S$ occurs, the measurement results are distorted, because the values ($I_B + I_S$) and ($I_M + I_S$) are measured instead of the true values $I_B$ and $I_M$. The distortion of the true values $I_A$ and $I_M$ increases as the intensity of the scattered light $I_S$ increases.

In the case of a very severe cataract, in very dark regions of the fundus, for instance the fovea, the scattered light may attain nearly the same intensities as the actual measurement signal reflected by the fundus. The method described thus has limits when parts are the fundus are illuminated by scattered light if the fundus brightness is very limited and therefore it is no longer possible to detect any fundus structures.

Measures for reducing the effect of scattered light on a cataract when using a fundus camera are known in the prior art from U.S. Pat. No. 7,147,328 A. It provides for manual adjustment options for the type and severity of a cataract. As an alternative to manual adjustment for the type and severity of a cataract, it is suggested that the cloudiness of the ocular lens be determined automatically. No specific procedure for automatically determining the severity of the cataract is provided. The imaging then occurs as a function of the severity of the cataract or cloudiness of the ocular lens. The more severe the cataract or the cloudier the eye lens, the greater the reduction made in the illumination brightness of a xenon lamp and in the output amplification in the blue channel of an imaging color image sensor should be. In this manner the scattered light saturation of the image taken is to be reduced.

It is a drawback of the suggested measure that by reducing the illumination brightness at the same exposure time, the image taken becomes darker, which has a negative impact on the contrast. If, for the sake of compensation, the exposure time is extended, the motion blur in the image increases due to unavoidable eye movements. In addition, diminishing the blue portion of light during imaging distorts the color impression of the image. Furthermore, a cataract also scatters light at wavelengths other than blue. This portion of the scattered light degrades the image quality despite the suggested measures for reducing the scattered light.

DE 101 29 652 A1 describes an arrangement and a method for determining the two-dimensional distribution of fundus pigments, especially the macular pigment xanthophyll. Here, a two-dimensional reflection image of the retina is taken in a selected narrow band wavelength range. During its evaluation, location specific areas are established for determining the optical density and comparison values. The optical density of the fundus pigment at each fundus location provides a comparative intensity value for the reflection image from the negative logarithmic value of the quotient of the intensity value of the reflection image at this fundus location. Even with this solution, it is a drawback that occurring scattered light leads to distortions of the measurements and thus of diagnosis results. No scattered light measurement and/or reduction in its effect is provided here.

Another solution for automatically determining the severity of a cataract in an eye is described in DE 10 2007 053 386 A1, in which the images of a section of an eye that are impacted by the scattered light are produced with undistorted color impression and the scattered light portion is determined. In this case, a light pattern that has at least one bright and one dark area is produced in the eye, at least a part of the dark area is imaged in a scattered light image and the intensities are integrated to create a cataract severity value. If the scattered light image is taken by use of a camera in a space-resolved manner, this represents a scattered light distribution that may be interpreted as distribution of cataract severity values. The spectrum and the brightness of an adapted illumination is adjusted for subsequent imaging as a function of the determined scattered light distribution and/or the cataract severity value.

Also suggested in DE 10 2007 047 300 A1 is a solution for determining the optical density of the macular pigment xanthophyll on the ocular fundus, using a determination based on reflection, in which solution the measurement results are not affected by interfering light, especially individual scattered light from the anterior ocular media. In this case only part of the ocular fundus is illuminated and the intensity of the interfering light from the non-illuminated area is measured in addition to the reflection light from illuminated areas. The measured value is used as a correction variable for calculating the optical density of the macular pigment.

In this case, it is a drawback that, just as in the solution described in the foregoing, one or a plurality of field stops must be present that are advantageously arranged to be able to pivot into and out of the illumination beam or measurement beam path. Such field stops entail additional costs. In addition, in this method at least two images of the fundus must be made and processed. Retrofitted integration into fundus cameras already available is not possible, or is only possible at great expense.

In addition to the lack of options to correct the scattered light for the images taken of the fundus, the solutions known from the prior art have the following other drawbacks:
  Devices are needed for compensating the distortions;
  In addition to the luminous field diaphragm present in every fundus camera, shading units for limiting image field illumination are need;
  Information in the fundus image may be lost due to the shading units.
  Additional fundus images are needed for determining the information about the scattered light.

Not only is the increased complexity of the technical equipment associated with additional costs, but it also means that operating such equipment is more complicated, which may then have a negative impact on the reliability and/or accuracy of the measurements.

SUMMARY OF THE INVENTION

A relative or absolute measurement of the scattered light is desirable in order to be able to evaluate for instance whether a cloudy human eye lens should be replaced by an artificial intraocular lens. A relative or absolute measurement of the scattered light would also be desirable for the solutions known according to the prior art and described in the foregoing because this would permit the effect of the scattered light on the results to be eliminated. The underlying object of the invention is to develop a solution with which the relative and the absolute quantity of scattered light may be measured when the images of the ocular fundus are being realized. The solution should preferably be based on a digital fundus camera that has a simple technical structure and is as simple as possible to operate in order to ensure that the measured values found are highly accurate, reliable, and reproducible.

This object is attained using the inventive method for realizing ocular fundus images that are corrected for scattered light using a digital fundus camera, in which method, corresponding to the method steps:
  a) the ocular fundus is illuminated, and,
  b) an image of the ocular fundus is realized in which the imaged surface area is larger than the illuminated surface area in that in the image of the ocular fundus realized in method step b) the scattered light intensity is determined and is used for a correction, in that:
  c) measurement points for determining the scattered light intensity are defined in the non-illuminated area of the fundus;
  d) after "outliers" have been eliminated, the values of the scattered light intensity determined at said measurement points are averaged; and
  e) the average scattered light intensity thus determined is subtracted from the intensity values of the realized fundus image in order to correct said image of the fundus realized in method step b).

The inventive method is based on the use of a digital fundus camera and realizes ocular fundus images that are corrected for scattered light. To this end, the scattered light intensity on the fundus is determined and used to correct the realized fundus images. In principle the suggested solution may be carried over to other methods of realizing fundus images and is not limited to the use of a digital fundus camera.

The invention shall be explained in greater detail in the following using exemplary embodiments.

DETAILED DESCRIPTION

In the inventive method for realizing ocular fundus images that are corrected for scattered light using a digital fundus camera, according to the method steps:
  a) the ocular fundus is illuminated, and
  b) an image of the ocular fundus is realized in which the imaged surface area is larger than the illuminated surface area.

In the image of the ocular fundus realized in method step b), the scattered light intensity is determined and used for a correction, in that:
  c) measurement points for determining the scattered light intensity are defined in the non-illuminated area of the fundus,
  d) after "outliers" have been eliminated, the values of the scattered light intensity determined at said measurement points are averaged, and
  e) the average scattered light intensity thus determined is subtracted from the intensity values of the realized fundus image in order to correct said image of the fundus realized in method step b).

One requirement for performing the inventive method is to use a fundus camera that offers the option for the imaged field of view to be larger than the illuminated field of view. This is the case, for instance, with fundus cameras that provide the option of being able to image different angle ranges without optical enlargement.

In accordance with the invention, according to the method steps:
  a) the ocular fundus is illuminated at an illumination angle $\beta$, and
  b) an image of the ocular fundus is realized at a field of view angle $\alpha$, wherein $\beta<\alpha$.

Most fundus cameras offer the option of making images with different illumination angles. Typically images may be made with a 30° aperture angle or with a 45° aperture angle. The suggested method is based on the idea that the fundus is illuminated at an angle of 30° but the larger area of the fundus is imaged by the sensor at 45°. However, the inventive method is not limited to these two angles, but instead may even be used for other angles in the same manner.

Figure 1:
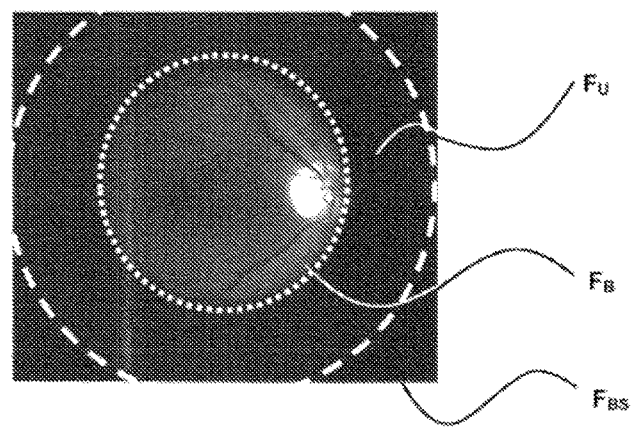
FIG. 1 is a fundus image in which the imaged surface area is larger than the illuminated surface area.

In this regard, FIG. 1 depicts an image of a fundus in which the imaged surface area is larger than the illuminated surface area. The illuminated surface area is labelled $F_B$ and the non-illuminated surface area is labelled $F_U$. The imaged surface area $F_A$ thus corresponds to the sum of the two surfaces $F_B$ and $F_U$. The total rectangular surface area represents the surface area $F_{BS}$ of the image sensor.

In an ideal case, i.e. without any occurring scattered light, the illuminated surface area $F_B$ would be imaged on the image sensor in front of a black background. Since fewer or more scattering particles are present in the anterior ocular media depending on the severity of the cataract, the illumination light is scattered on these particles, both in the direction of the fundus and in the opposite direction. The scattering of the illumination light towards the retina occurs in two dimensions and at a wide angle so that the entire surface area $F_A$ to be imaged is illuminated.

The scattered light that occurs increases as the severity of the cataract increases, which leads to the actually non-illuminated surface area $F_U$ being illuminated with increasingly higher intensity.

Figure 2:
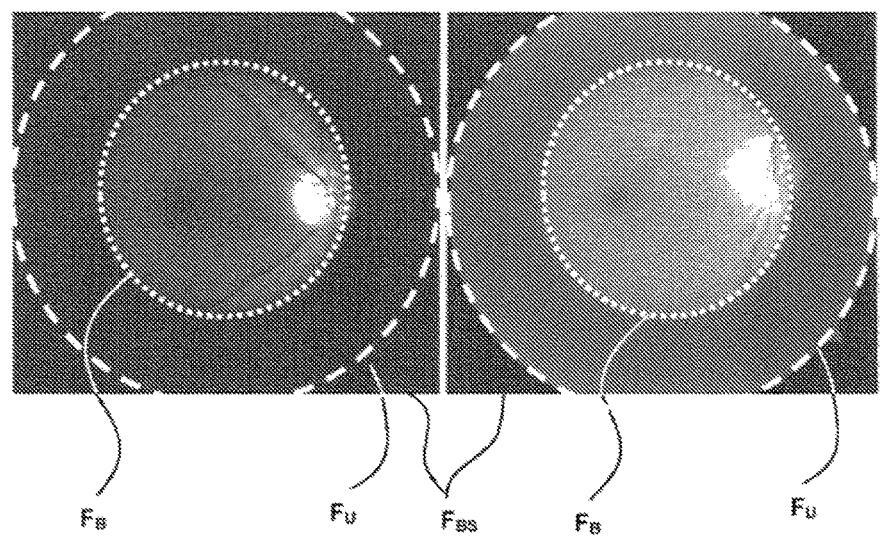
FIG. 2 is the fundus images of two eyes in which the cataracts are of differing severity.

To illustrate this, FIG. 2 provides fundus images of two eyes in which the cataracts are of different severity. While the fundus image on the left shows an eye having a minor or no cataract (that is, little scattered light), the cataract in the eye shown in the fundus image on the right is severe, which may be seen from the greater proportion of scattered light.

The light scattered towards the retina (forward) may be interpreted like additional illumination with a very wide illumination angle. This leads to the illuminated surface area $F_B$ being further illuminated and the actual non-illuminated surface area $F_U$ being illuminated.

In addition, a worsening of the signal-to-noise ratio (SNR) is caused by the direct back-scattering of light on particles of the anterior ocular media in the observation beam path. This is expressed inter alia in a worsening of contrast. As may be seen from the fundus image on the right in FIG. 2, structures are no longer imaged as clearly because of this.

The fundus image is overlaid by interfering scattered light in two dimensions. Thus, due to this scatter effect, the intensities $I_B$ of the fundus image that are present is overlaid by the constant scatter intensity $I_S$, which is an addition. If the scatter intensity $I_S$ is known, it is possible to calculate the corrected fundus image with the intensities $I_B$ by subtracting the scatter intensity $I_S$ from the intensities of the fundus image affected by scatter.

If it is assumed that the fundus image is overlaid in two dimensions by the interfering scattered light, an equivalent for this may be determined in the outer area of the fundus image and carried over to the entire fundus image. It may be seen from the image on the right in FIG. 2 that the brightness in the outer area is nearly uniform.

In addition, no more structures are detectable in the outer area starting at a certain distance from the transition region from the illuminated to the non-illuminated area. This means that the scattering is very uniform and that the average value in the actually non-illuminated outer area represents a good measure for the average absolute scattered light. In particular the averaging is also robust relative to noise effects over a large range.

For determining the scattered light intensity in accordance with method step c), at least 5 measurement points are used according to an example embodiment, preferably 10 measurement points are used according to another example embodiment, and especially preferably 20 measurement points distributed as uniformly as possible are defined in the non-illuminated area of the fundus are used according to a further example embodiment.

To be able to define the measurement points in accordance with method step c), it is necessary for both the non-illuminated and also the imaged area of the fundus either to be known or detected.

It should be noted that, despite constant illumination parameters, the size of the illuminated area of the fundus may vary. This is highly dependent on the patient's ametropia. Therefore it appears reasonable to maintain a safety margin from the transition region between the illuminated area and the non-illuminated area when the scattered light intensity is determined in the non-illuminated area.

If the eye to be examined suffers from ametropia, the ametropia should be taken into account during the determination of the non-illuminated area of the fundus. Since as a rule the ametropia to be examined must be known in order to be able to focus the fundus camera on the ocular fundus that is to be imaged, the non-illuminated area of the fundus should also be known. For fundus cameras in which focusing on the fundus takes place automatically, i.e. without the knowledge of the specific ametropia, it is necessary to detect the non-illuminated area of the fundus.

The non-illuminated area of the fundus, especially its edge, is detected using known image processing methods that are primarily adapted for detecting geometric shapes of a light screen and are based, for instance, on a Hough transformation.

In an example embodiment, a safety margin for the measurement points to be defined in method step c) is taken into account, both to the illuminated area of the fundus and also to the outer edge of the imaged area. This can minimize the occurrence of so-called "outliers." The safety margin to be selected may be smaller if the non-illuminated and the imaged area of the fundus are known precisely or were detected using image processing methods.

In accordance with a first advantageous example embodiment of the inventive method, in method step c), instead of individual measurement points for determining the scattered light intensity, a measurement area in the non-illuminated area of the fundus may be defined that, for example, has the shape of a circular ring. The determination of the scattered light intensity in accordance with method step d) is then accomplished using integration across the defined measurement area.

In accordance with example embodiments of the invention, the safety margin is also provided in the form of an angle, wherein $\delta_1$ characterizes the safety margin to the illuminated area of the fundus or the illumination angles $\beta$, and $\delta_2$ characterizes the safety margin to the outer edge of the imaged area or to the field of view angle $\alpha$. The circular ring $\gamma$ is thus defined by the following outer limits:

$(\beta+\delta_1)$ and
$(\alpha-\delta_2)$.

The safety margins $\delta_1$ and $\delta_2$ may assume the same or different values.

Figure 3:
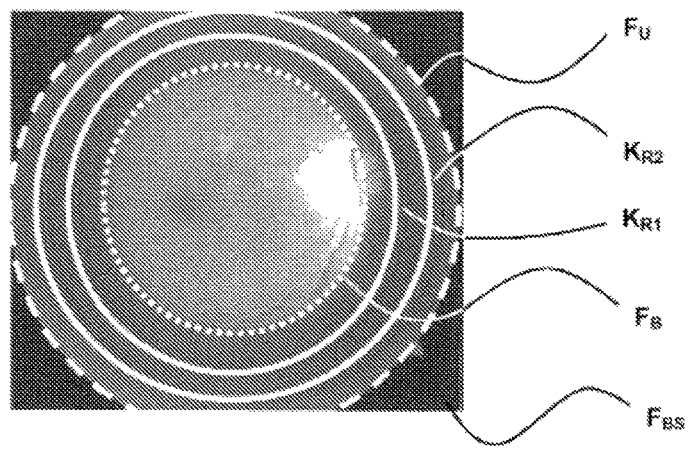
FIG. 3 is a fundus image in which the measurement area for determining the scattered light intensity in the non-illuminated area is marked.

FIG. 3 provides a fundus image in which the measurement area for determining the scattered light intensity in the non-illuminated area is marked. In this case, as well, the imaged surface area $F_A$ equals the sum of the illuminated surface area $F_B$ and the non-illuminated surface area with $F_U$. For determining the scattered light intensity in the non-illuminated area $F_U$, a measurement area is defined that is characterized by the two circular rings $K_{R1}$ and $K_{R2}$.

Here, as well, it is possible to use the method steps described in the foregoing with respect to knowing both the non-illuminated and also the imaged area of the fundus, or detecting them, and to take into account the ametropia of the eye to be examined and maintain a safety margin.

The absolute intensity of the scattered light correlates to the quantity and size of the scattering particles in the anterior media of the human eye and thus, e.g., to the severity of cataract. Moreover, the intensity $I_S$ of the scattered light is approximately a linear function of the intensity $I_{BB}$ of the flash lamp.

In accordance with one example embodiment of the inventive method, the average (absolute) scattered light intensity determined in method step e) is related to the intensity of the flash lamp of the fundus camera and define a measure for the severity of a cataract in the eye to be examined as relative scattered light intensity.

While the portion relative to the entire light intensity is understood to be a relative portion of the scattered light, the absolute portion is the absolute quantity of the scattered light.

In this context, it is advantageous to store the relative scattered light intensity and compare it to prior and/or later measured values in order to be able to draw conclusions therefrom regarding the severity of a cataract and any changes.

The determined magnitude of the scattered light may also be compared to age-based characteristics in order to be able to detect deviations. Major deviations from an age-based characteristic may provide indications of an eye disorder that is present.

The absolute intensity of the scattered light correlates to the quantity and size of the light scattering particles in the anterior media of the human eye and thus also, e.g., to the severity of a cataract. Moreover, the scattered light has an approximately linear relationship, i.e., if the back-scatter is ignored, to the intensity of the flash lamp and is thus a measure of the severity of the cataract. The inventive method thus permits the severity of the cataract to be measured with a digital fundus camera.

In addition, it is advantageous to convert the value of the relative scattered light intensity to diagnostic values for other cataract measurement methods, such as for instance the values of a Scheimpflug camera or a slit lamp.

A mathematical regression may for example be used for converting the values of the relative scattered light intensity to diagnostic values for other cataract measurement methods.

In accordance with another example embodiment of the inventive method, the ocular fundus image realized in method step b) is checked with respect to maintaining the minimum standard of image quality prior to the further processing, wherein these minimum standards are attained with respect to dynamics and brightness if typical structures such as arteries, veins, pupils, or the area of the macula are detectable in the illuminated area.

The minimum standard of image quality has been attained with respect to correct orientation of the fundus camera if the fundus image has homogeneous illumination.

If the minimum standards of image quality are not maintained, the image of the ocular fundus realized in method step b) is discarded and the scattered light intensity is not determined.

In such a case, the operator of the fundus camera receives, for example, an indication that quality criteria have not been satisfied and reproducibility is reduced for poor image quality.

Figure 4:
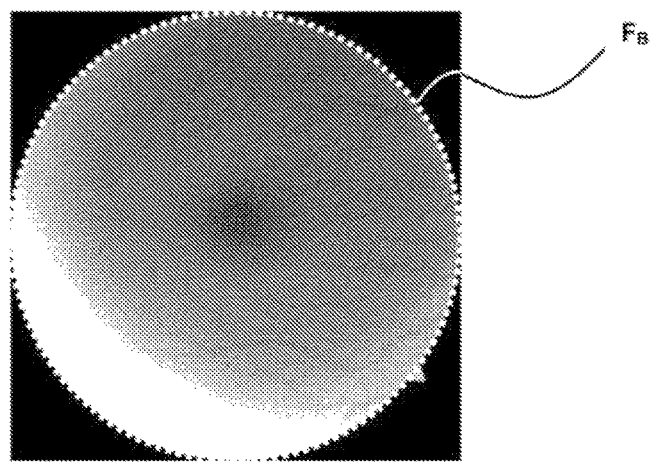
FIG. 4 is a fundus image in which the minimum standard of image quality is not maintained with respect to dynamics and brightness.

In this regard, FIG. 4 is a fundus image in which the minimum standard of image quality is not maintained in terms of dynamics and brightness. In contrast to the previous images, this image includes only the illuminated surface $F_B$, since only this illuminated surface is examined with respect to maintaining the minimum standards. However, the minimum standard for image quality with respect to dynamics and brightness is not maintained here, since the illuminated surface area $F_B$ is over-illuminated at the bottom left.

With the inventive solution, a method is provided with which it is possible to realize ocular fundus images that are corrected for scattered light using a digital fundus camera. With the suggested method, the relative and absolute quantity of scattered light may be measured during the realization of fundus images. Thus the present invention makes it possible to measure and evaluate the severity of the cataract with a digital fundus camera.

The solution is for example based on a digital fundus camera that is adequately known from the prior art and has a simple technical structure and is relatively simple to operate. Using it, it is possible for the determined measurement values to be highly accurate, reliable, and reproducible.

REFERENCE LIST $F_B$ Illuminated surface area
$F_U$ Non-illuminated surface area
$F_A$ Imaged surface area
$F_{BS}$ Surface area of the image sensor
$I_S$ Scatter intensity
$I_B$ Intensity of the fundus image in the illuminated area
$I_{BB}$ Flash intensity of the illumination light
$K_{R1}$, $K_{R2}$ Circular rings for defining the measurement area
$\alpha$ Field of view angle
$\beta$ Illumination angle
$\gamma$ Angle extension of circular ring
$\delta_1$, $\delta_2$ Safety margins

The invention claimed is:

1. A method for realizing ocular fundus images that are corrected for scattered light using a digital fundus camera, the method comprising:
   a) illuminating the ocular fundus by application of an illumination source located within the digital fundus camera and directed through optics of the digital fundus camera into an eye and onto the ocular fundus, and
   b) capturing a digital image of the ocular fundus through the optics of the digital fundus camera in which an imaged surface area of the ocular fundus is larger than an illuminated surface area of the ocular fundus,
   wherein in the digital image of the ocular fundus realized in b) a scattered light intensity is determined and is used for a correction, the method further comprising
   c) defining, by application of the digital fundus camera, measurement points or a measurement area, the measurement points or the measurement area for determining the scattered light intensity being located in a non-illuminated area of the ocular fundus adjacent to or surrounding the illuminated area of the ocular fundus;
   d) in the case of measurement points in the non-illuminated area of the ocular fundus, eliminating outliers and after the outliers have been eliminated, averaging values of scattered light intensity determined at said measurement points to determine an averaged scattered light intensity by application of the digital fundus camera; and
   e) using the average scattered light intensity thus determined to correct said image of the ocular fundus realized in method step b) or to define the severity of a cataract by application of the digital fundus camera.

2. The method in accordance with claim 1, further comprising: a) illuminating the ocular fundus at an illumination angle β, and b) capturing a digital image of the ocular fundus at a field of view angle α, wherein β<α.

3. The method in accordance with claim 1, further comprising, for determining the scattered light intensity in accordance with method step c), utilizing at least 5 of the measurement points.

4. The method in accordance with claim 3, further comprising, utilizing at least 10 of the measurement points.

5. The method in accordance with claim 3, further comprising utilizing at least 20 of the measurement points and distributing the measurement points as uniformly as possible in the non-illuminated area of the fundus.

6. The method in accordance with claim 1, wherein for defining the measurement points in accordance with method step c), it is necessary for both the non-illuminated and also the imaged area of the fundus either to be known or detected.

7. The method in accordance with claim 6, further comprising, during the determination of the non-illuminated area of the fundus, taking into account the ametropia of the eye to be examined.

8. The method in accordance with claim 6, further comprising detecting an edge of the non-illuminated area of the fundus using image processing methods.

9. The method in accordance with claim 8, wherein the image processing methods used are adapted for detecting geometric shapes of a light screen.

10. The method in accordance with claim 8, wherein the image processing methods used are based on a Hough transformation.

11. The method in accordance with claim 1, further comprising taking into account a safety margin for the measurement points to be defined in method step c), both to the illuminated area of the fundus and also to the outer edge of the imaged area.

12. The method in accordance with claim 1, further comprising, in method step c), wherein the measurement area is used and the measurement area in the non-illuminated area of the fundus has the shape of a circular ring.

13. The method in accordance with claim 12, wherein the measurement area in the shape of a circular ring that is defined for determining the scattered light intensity has a safety margin $δ_1$ to an illumination angle β and a safety margin $δ_2$ to a field of view angle α.

14. The method in accordance with claim 12, further comprising, in method step d) using intergration to determine the scattered light intensity across the measurement area.

15. The method in accordance with claim 1, further comprising checking the ocular fundus image realized in method step b) with respect to maintaining a minimum standard of image quality prior to further processing.

16. The method in accordance with claim 15, wherein the minimum standard of image quality is attained with respect to dynamics and brightness if the structures of the fundus are detectable.

17. The method in accordance with claim 15, wherein the minimum standard of image quality has been attained with respect to correct orientation of the fundus camera if the fundus image has homogeneous illumination.

18. The method in accordance with claim 15, wherein, if the minimum standards of image quality are not maintained, the image of the ocular fundus realized in method step b) is discarded.

19. The method in accordance with claim 1, further comprising:
e) using the average scattered light intensity thus determined in order to correct said digital image of the fundus realized in method step b) by subtracting the average scattered light intensity thus determined from the intensity values of this fundus image.

20. The method step in accordance with claim 1, further comprising:
e) using the average scattered light intensity thus determined in order to define the severity of a cataract, by relating average (absolute) scattered light intensity thus determined to an intensity of a flash lamp of the fundus camera and defining a measure for the severity of a cataract in the eye to be examined as relative scattered light intensity.

21. The method in accordance with claim 20, further comprising storing the relative scattered light intensity and comparing the relative scattered light intensity to prior measured values, later measured values or both prior measured values or later measured values to draw conclusions therefrom regarding the severity of a cataract and any changes.

22. The method in accordance with claim 20, further comprising converting the value of the relative scattered light intensity to diagnostic values for other cataract measurement methods.

23. The method in accordance with claim 22, further comprising converting the value of the relative scattered light intensity to diagnostic values to values of a Scheimpflug camera or a slit lamp.

24. The method in accordance with claim 20, further comprising using a mathematical regression for converting the values of the relative scattered light intensity to diagnostic values for other cataract measurement methods.

25. The method in accordance with claim 12, wherein for defining the measurement points in accordance with method step c), it is necessary for both the non-illuminated and also the imaged area of the fundus either to be known or detected.

26. The method in accordance with claim 25, further comprising, during the determination of the non-illuminated area of the fundus, taking into account the ametropia of the eye to be examined.

27. The method in accordance with claim 25, further comprising detecting an edge of the non-illuminated area of the fundus using image processing methods.

28. The method in accordance with claim 27, wherein the image processing methods used are adapted for detecting geometric shapes of a light screen.

29. The method in accordance with claim 27, wherein the image processing methods used are based on a Hough transformation.

* * * * *

UNITED STATES PATENT AND TRADEMARK OFFICE
CERTIFICATE OF CORRECTION

PATENT NO. : 10,130,248 B2
APPLICATION NO. : 14/890365
DATED : November 20, 2018
INVENTOR(S) : Thomas Mohr et al.

It is certified that error appears in the above-identified patent and that said Letters Patent is hereby corrected as shown below:

In the Claims

Column 8, Line 41, delete "eve" and insert --eye--

Signed and Sealed this
Twenty-second Day of January, 2019

Andrei Iancu
*Director of the United States Patent and Trademark Office*